(12) United States Patent
Withnall et al.

(10) Patent No.: US 6,871,525 B2
(45) Date of Patent: Mar. 29, 2005

(54) METHOD AND APPARATUS FOR TESTING FOOTBALL HELMETS

(75) Inventors: Christopher R. P. Withnall, Nepean (CA); Timothy D. Bayne, Nepean (CA)

(73) Assignee: Riddell, Inc., Chicago, IL (US)

( * ) Notice: Subject to any disclaimer, the term of this patent is extended or adjusted under 35 U.S.C. 154(b) by 0 days.

(21) Appl. No.: 10/462,313

(22) Filed: Jun. 13, 2003

(65) Prior Publication Data

US 2004/0074283 A1 Apr. 22, 2004

Related U.S. Application Data

(60) Provisional application No. 60/388,691, filed on Jun. 14, 2002.

(51) Int. Cl.[7] .................................................. G01M 7/00
(52) U.S. Cl. ....................................................... 73/12.14
(58) Field of Search .............................. 73/12.04, 12.09, 73/12.14

(56) References Cited

U.S. PATENT DOCUMENTS

| | | | |
|---|---|---|---|
| 403,676 A | 5/1889 | Keep | |
| 1,636,234 A | 7/1927 | Klopsteg | |
| 2,430,876 A | 11/1947 | Hodges | |
| 3,903,971 A | * 9/1975 | Watanabe | 173/37 |
| 3,945,587 A | * 3/1976 | Willey et al. | 242/384.5 |
| 4,442,697 A | 4/1984 | Jones et al. | |
| 5,003,811 A | 4/1991 | Shannon et al. | |
| 5,285,687 A | 2/1994 | Ringel et al. | |
| 5,441,269 A | * 8/1995 | Henwood | 473/220 |
| 5,589,628 A | 12/1996 | Braly | |
| 5,792,001 A | * 8/1998 | Henwood | 473/224 |
| 5,922,937 A | * 7/1999 | Kowalski et al. | 73/12.14 |
| 5,943,706 A | 8/1999 | Miyajima et al. | |

OTHER PUBLICATIONS

*Hot Off the Press*, Jun. 16, 2002, 2 pages, First Technology Safety Systems, Plymouth, MI.

* cited by examiner

*Primary Examiner*—Max Noori
(74) *Attorney, Agent, or Firm*—Wallenstein Wagner & Rockey, Ltd.

(57) ABSTRACT

A method and apparatus for testing a football helmet utilizes a weighted pendulum arm to impart an impact force upon the helmet. Linear head acceleration and rotational head acceleration caused by the impact force is measured and a Head Impact Power Index is computed and used as a standard to judge the ability and effectiveness of the football helmet in preventing injury to a football player.

33 Claims, 11 Drawing Sheets

METHOD AND APPARATUS FOR TESTING FOOTBALL HELMETS

RELATED APPLICATION

This application claims the benefits of U.S. Provisional Patent Application Ser. No. 60/388,691, filed Jun. 14, 2002, entitled Method and Apparatus for Testing Football Helmets.

BACKGROUND OF THE INVENTION

1. Field of the Invention

The invention relates to a method and apparatus for testing football helmets.

2. Description of the Related Art

Various activities, such as contact sports, and in particular the sport of football, require the use of helmets to attempt to protect participants from injury to their heads due to impact forces that may be sustained during such activities. Various types of helmets have been in use in the sport of football, ever since individuals began wearing helmets to attempt to protect their heads many years ago. Typically, these helmets have included: an outer shell, generally made of an appropriate plastic material, having the requisite strength and durability characteristics to enable them to be used in the sport of football; some type of shock absorbing liner within the shell; a face guard; and a chin protector, or chin strap, that fits snugly about the chin of the wearer of the helmet, in order to secure the helmet to the wearer's head, as are all known in the art.

Various standards have been proposed and used for testing football helmets, such as the standards promulgated by the National Operating Committee on Standards for Athletic Equipment ("NOCSAE"). Prior test standards and tests for football helmets were directed to measuring linear head accelerations, when the shell of the helmet has an impact force imparted upon it. Typically, the football helmet was suspended above an anvil disposed on a laboratory floor, and the helmet was permitted to drop, or free-fall, until it struck the anvil. Thus, prior test standards and test methods and equipment only considered linear head accelerations when testing football helmets. Football helmets were not tested or evaluated as to their ability to protect against not only linear head acceleration, but also rotational head acceleration, caused by impact forces upon the helmet.

While it is the desire and goal that a football helmet prevent injuries from occurring, it should be noted that due to the nature of the sport of football in particular, no protective equipment or helmet can completely, totally prevent injuries to those individuals playing the sport of football. It should be further noted that no protective equipment can completely prevent injuries to a player, if the football player uses his football helmet in an improper manner, such as to butt, ram, or spear an opposing player, which is in violation of the rules of football. Improper use of a helmet to butt, ram, or spear an opposing player can result in severe head and/or neck injuries, paralysis, or death to the football player, as well as possible injury to the football player's opponent. No football helmet, or protective helmet can prevent head, chin, or neck injuries a football player might receive while participating in the sport of football. It is believed that no helmet can, or will ever, totally and completely prevent head injuries to football players.

The method and apparatus for testing football helmets of the present invention, when compared to previously proposed methods and apparatus for testing football helmets, has the advantage of being capable of delivering and measuring not only the ability of the helmet to protect against linear head acceleration, but also rotational head acceleration.

SUMMARY OF THE INVENTION

In accordance with the invention, the foregoing advantage is believed to have been achieved by the method and apparatus for testing football helmets of the present invention.

The method and apparatus for testing football helmets of the present invention, when compared with previously proposed methods and apparatus for testing football helmets, are believed to have the advantage of permitting the delivery and measurement of both linear and rotational head accelerations.

Figure 1:
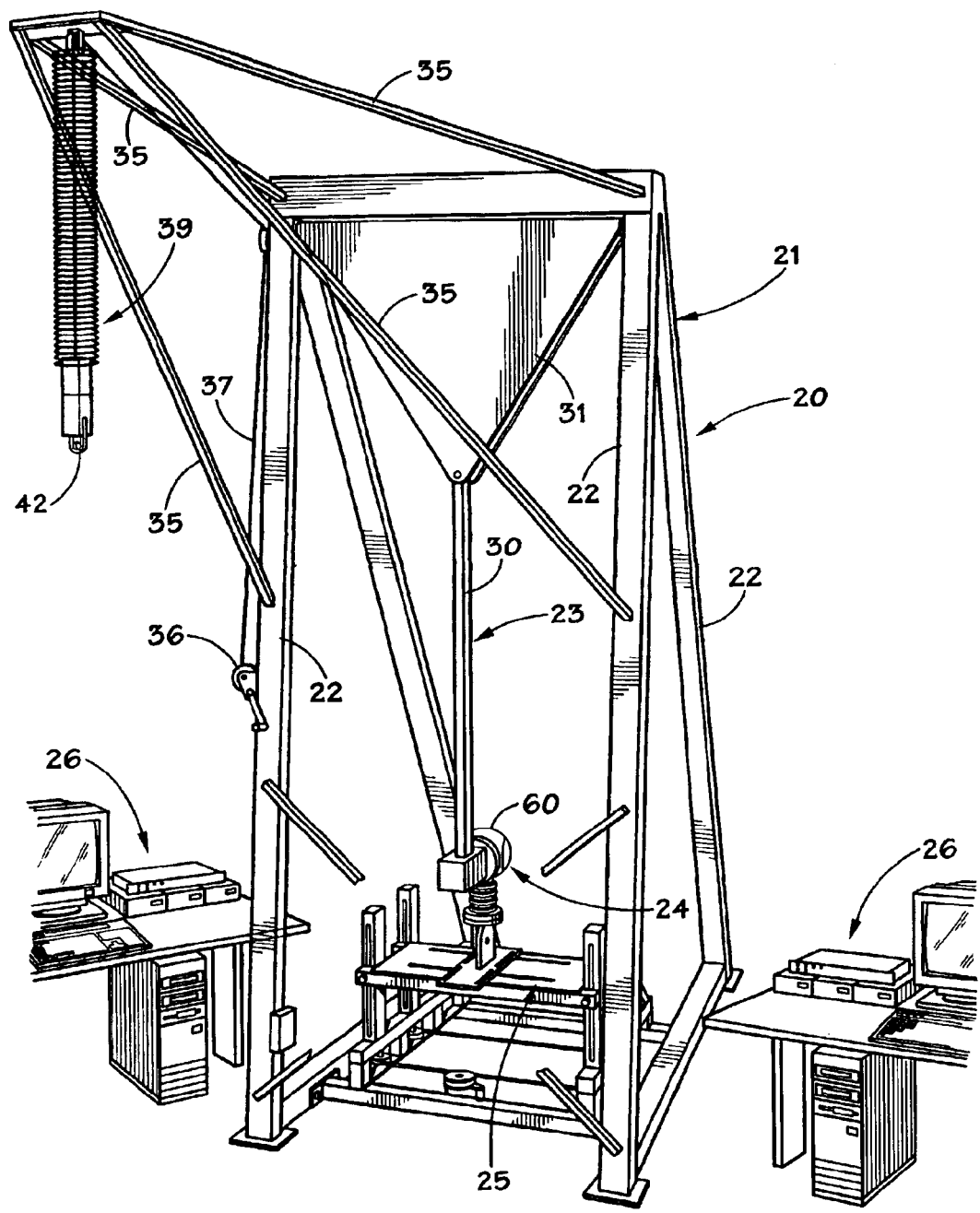
FIG. 1 is a perspective view of the preferred embodiment of a football helmet testing apparatus in accordance with the present invention.

While the invention will be described in connection with the preferred embodiments shown herein, it will be understood that it is not intended to limit the invention to those embodiments. On the contrary, it is intended to cover all alternatives, modifications, and equivalents, as may be included within the spirit and scope of the invention as defined by the appended claims.

DETAILED DESCRIPTION OF THE INVENTION

In general, the football helmet test apparatus 20 (FIG. 1) is capable of delivering a blow similar to those seen in head-to-head football collisions. A headform, or head-neck assembly, is mounted upon an adjustable platform, or base assembly, that allows any point on the head to be presented to a weighted pendulum. The impact face of the weighted pendulum has a spherical curvature, similar to that of a football helmet, and the impact face is covered with the same plastic as conventional football helmets. When football players' heads collide, there is considerable rebound as their helmets deflect from one another. Thus, the pendulum arm of the pendulum is designed to have the same lateral stiffness as of the head-neck assembly, whereby the impact head, or face, and pendulum will deflect away from each other in a glancing blow, as is the case when two helmeted football players' heads collide.

The testing method and test standard of the present invention are intended to supplement, but not replace, currently accepted football helmet standards and testing methods, such as: ASTM F429-97 Shock Attenuation Characteristics of Protective Headgear for Football; ASTM F717-89 Standard Specification for Football Helmets; NOCSAE DOC. 002-96 Standard Performance Specification for Newly Manufactured Football Helmets; and ASTM F1446-99 Standard Test Methods for Equipment and Procedures Used in Evaluating the Performance Characteristics of Protective Headgear.

Throughout this patent application, the following terms shall have the following definitions: "Hybrid III": A biofidelic anthropomorphic test device (ATD) corresponding in head and neck dimensions to a 50th percentile adult male, and commercially available from First Technology Safety Systems of Plymouth, Mich., 48170, www.ftss.com.

"Resultant linear acceleration": The vector sum of the individual linear X (forward), Y (lateral) and Z (vertical) headform accelerations, expressed in units of meters per second per second, or in G's. "Resultant rotational (or angular) acceleration": The vector sum of the individual rotational X (forward), Y (lateral), and Z (vertical) headform accelerations, expressed in units of radians per second per second.

"G": Dimensionless ratio of linear acceleration to the acceleration of gravity.

"Power Index (or Head Impact Power Index or HIP)": The maximum value of power, calculated as the instantaneous product of mass, acceleration and velocity plus the instantaneous product of moment of inertia, rotational acceleration and rotational velocity of the head, expressed in units of watts (W), or kilowatts (kW).

Figure 2:
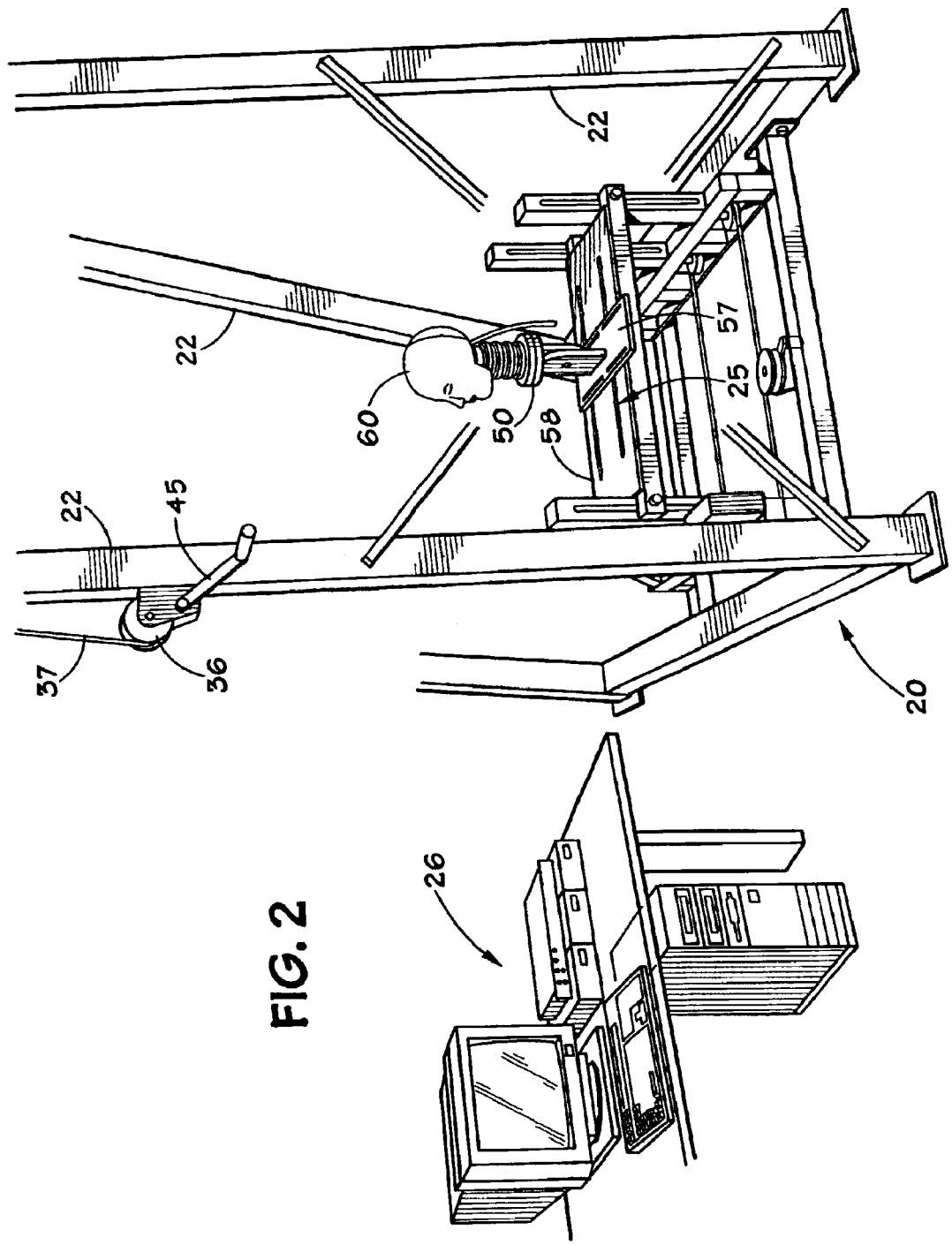
FIG. 2 is a partial, perspective view of the testing apparatus of FIG. 1.
Figure 3:
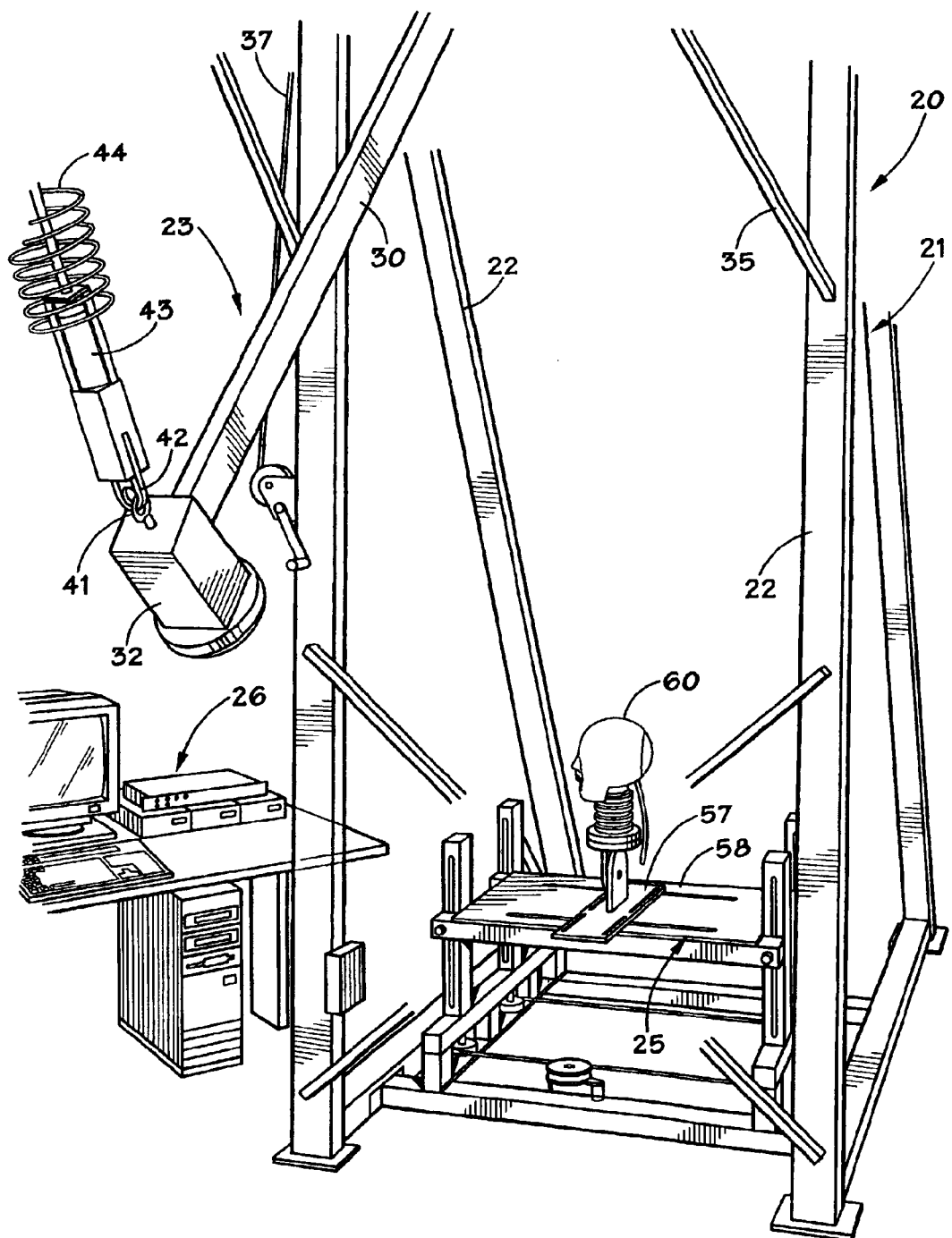
FIG. 3 is another partial, perspective view of the testing apparatus of FIG. 1.

With reference to FIGS. 1–3, the test apparatus 20 of the present invention is shown to generally comprise a frame assembly, or frame, 21 formed of a plurality of support members 22; a pendulum impactor 23 mounted for pivotal movement with respect to the frame 21; a headform-neck, or head-neck, assembly 24; a head base assembly 25 associated with frame 21; and suitable electronics for receiving and processing signals, as will be hereinafter described in greater detail, from accelerometers (not shown) disposed within the headform-neck assembly.

Still with reference to FIGS. 1–3, the frame members are made of any suitable material having the requisite strength and durability characteristics to function in test apparatus 20, and are preferably formed of metal such as a suitable steel or aluminum. The pendulum impactor 23 includes: a pendulum arm 30, a connector, or support plates, 31 attached to the upper end of arm 30; and a impact head, or face, 32. The support plates 31, which are attached to the upper end of pendulum arm 30 in any suitable manner, such as by nuts and bolts, are pivotally mounted between some of the vertical support members 22 of frame 21. Support plates 31 may have a triangular shape as shown in FIG. 1.

The pendulum arm 30 length, measured between the centerline of the impacting face 32 and the pivot axis 33, is preferably a minimum length of 200 cm. The impacting face 32 is preferably made of metal, and has a diameter of approximately 152 mm, ±10 mm.

Figure 13:
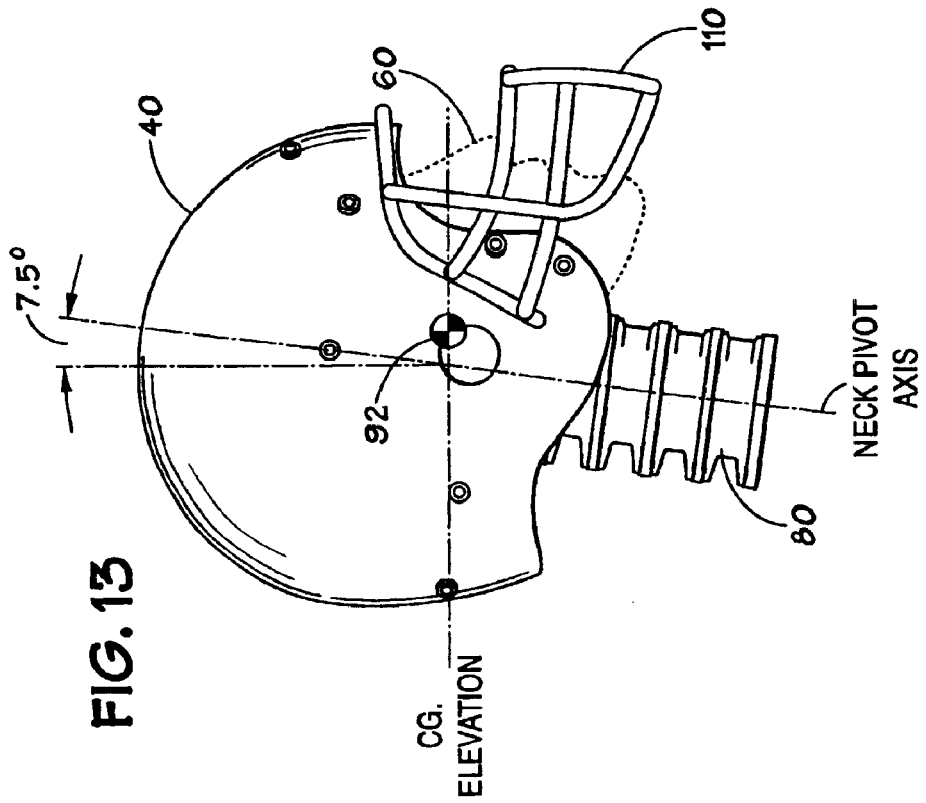
FIGS. 12 and 13 are side views of the headform of FIGS. 6 and 9, with football helmets mounted on the headforms, and illustrate the location of preferred impact locations utilized in testing football helmets with the method and apparatus of the present invention.
Figure 12:
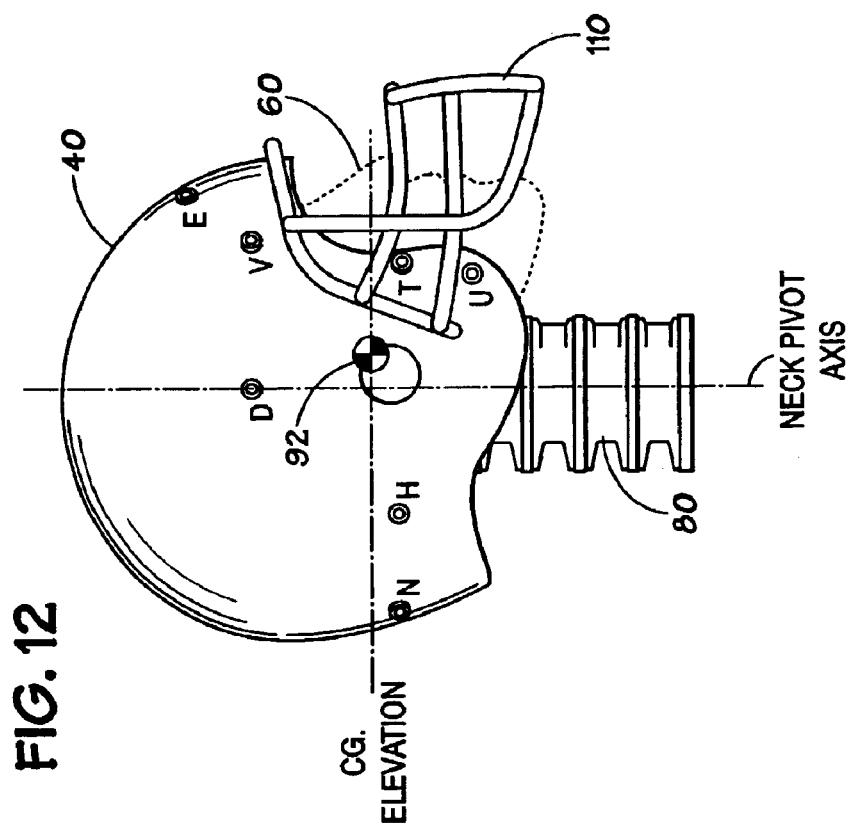

Typical, high range closing head-to-head impact speeds while playing the game of football are in the range of 10 m/s, and a rough estimation of typical impact energy at such impact speeds has been calculated to be 280 J. The movement of pendulum impactor 23 is intended to simulate a tackler's head, neck and partial torso mass, and is preferably 19 kg (effective mass measured at the impact face 32 with the pendulum arm 30 extended horizontal). Using 280 J as an energy guide, the 19 kg pendulum speed is preferably 5.4 m/s, measured at the impacting face 32. Preferably, the impact face 32 has a domed spherical outer surface 33 having a radius of curvature of approximately 127 mm±10 mm, which radius generally corresponds to the radius of curvature of the upper portion of a typical football helmet 40 (FIGS. 12 and 13).

The impact face 32 preferably has a 4 mm±2 mm thick layer 34 of polycarbonate plastic material having the same radius of curvature. This plastic material corresponds to the same plastic material of which the outer shell of helmet 40 is made. Of course, other plastic materials could be utilized, if they substantially correspond, or compare, to the material of which helmet 40 is made. Under a lateral force of 350 N±25 N, the impact face 32 shall be deflected 100 mm±10 mm, and this compares to force required to displace the head-neck assembly 24 the same distance.

Figure 4:
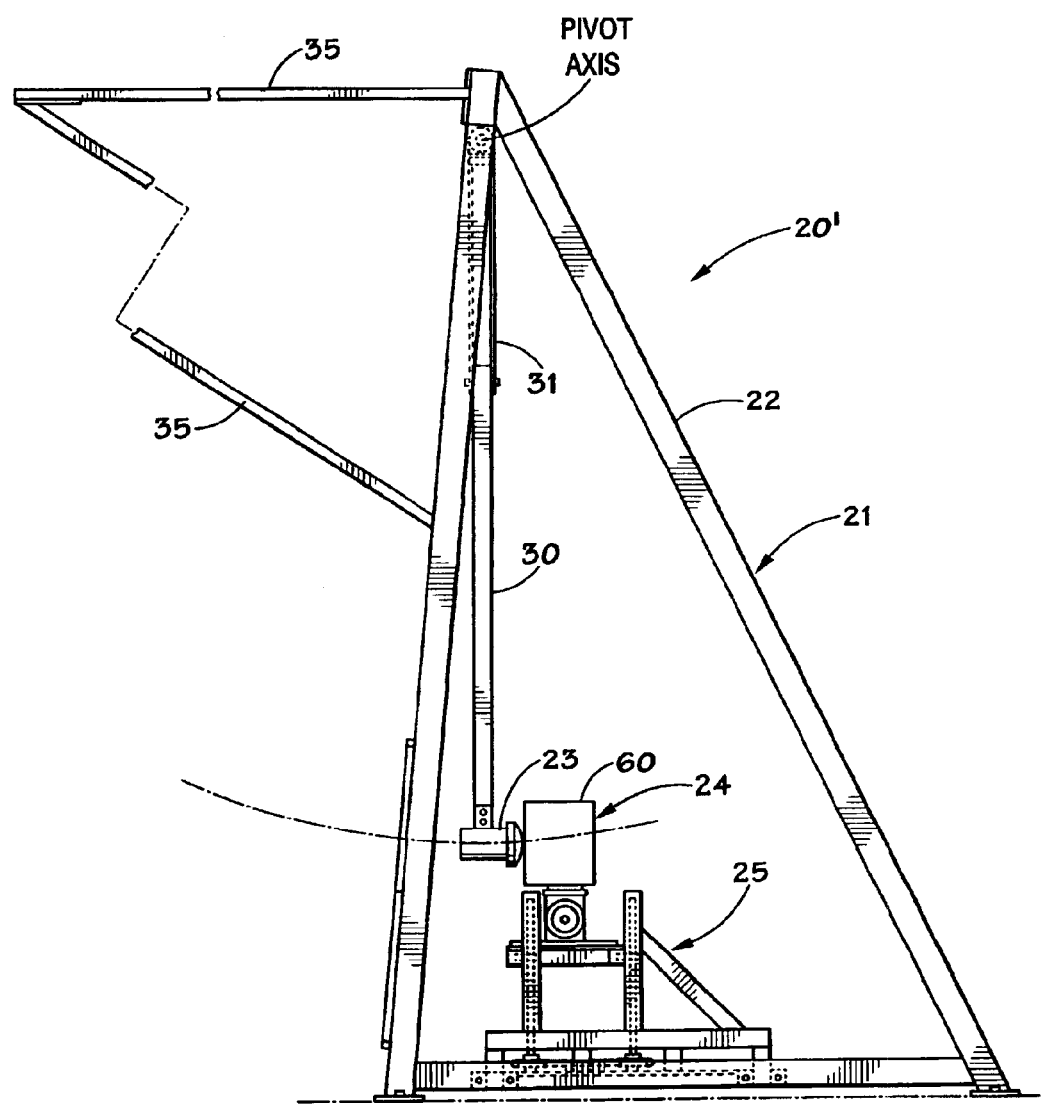
FIG. 4 is a side view of another embodiment of the testing apparatus of the present invention.
Figure 5:
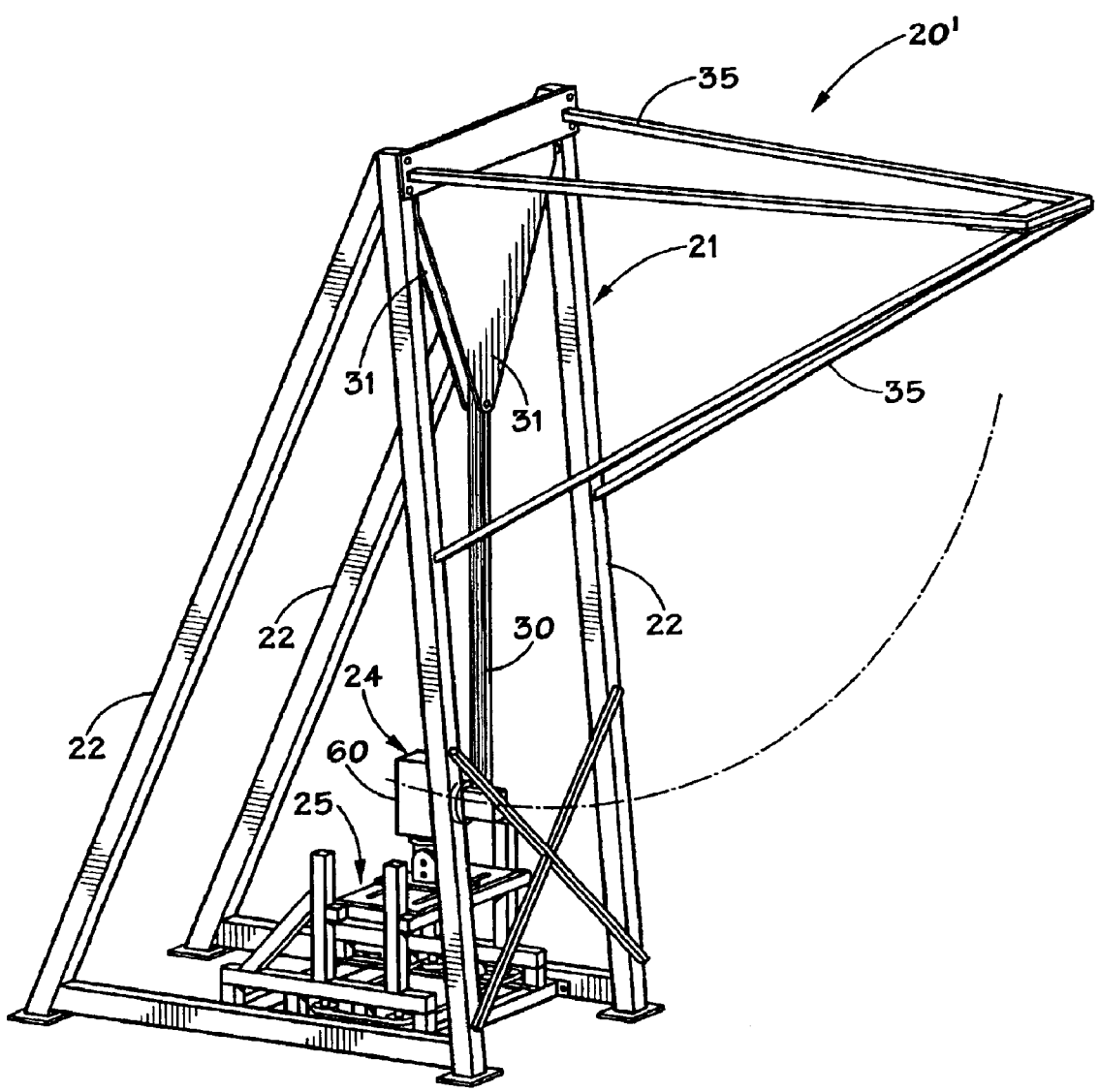
FIG. 5 is a perspective view of the testing apparatus of FIG. 4.
Figure 6:
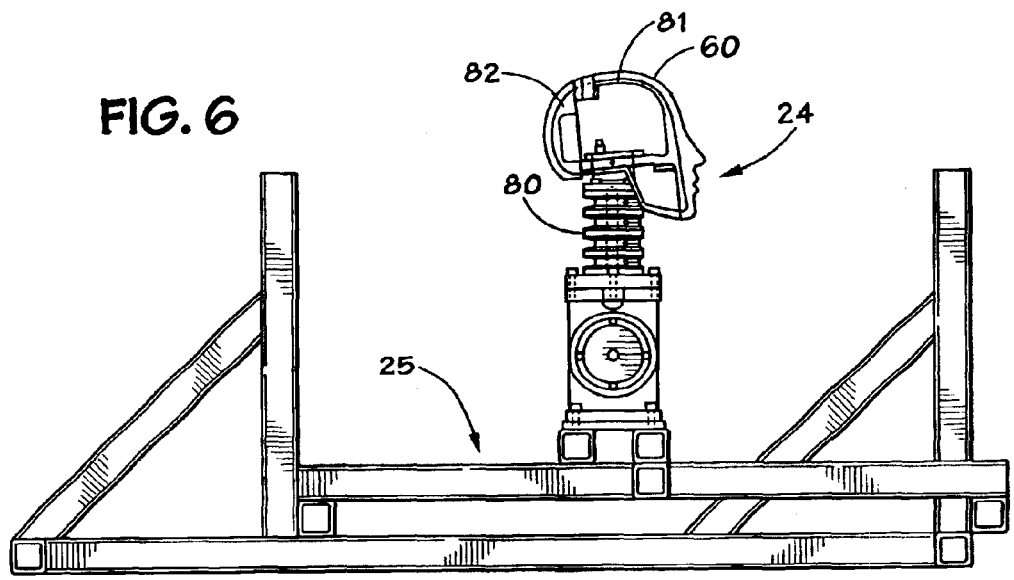
FIG. 6 is a side view of an adjustable head form platform used in the testing apparatus of FIG. 1 and FIG. 4.
Figure 7:
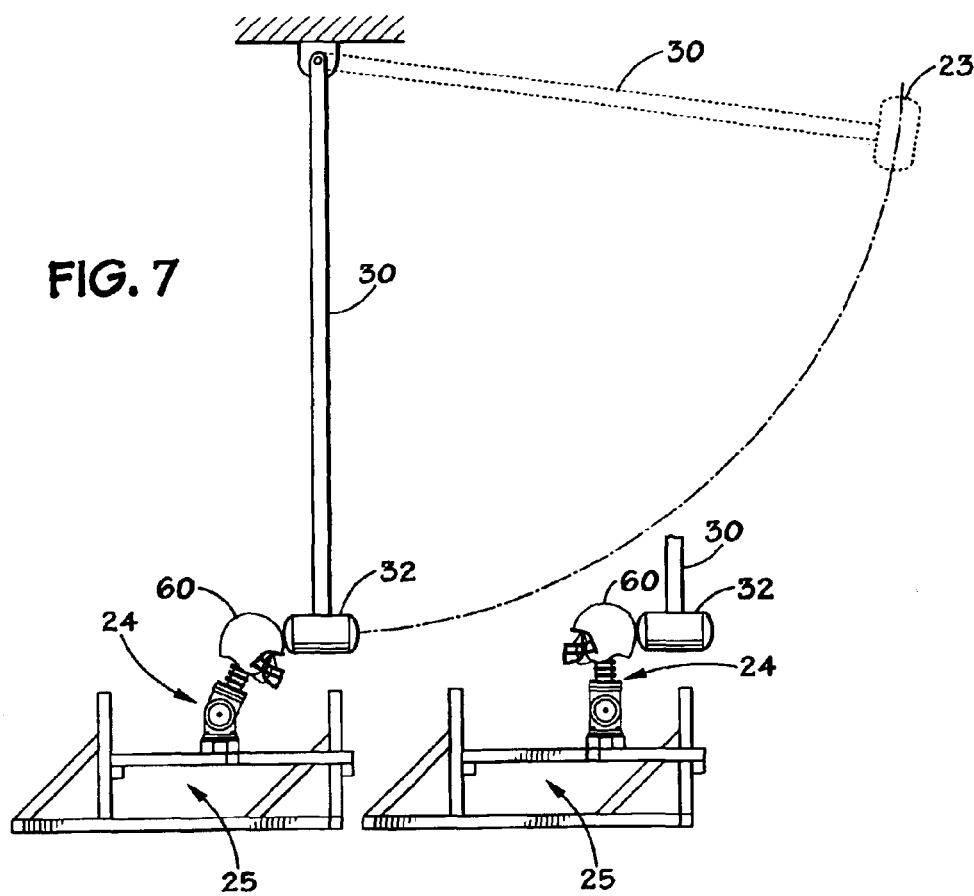
FIG. 7 is a schematic side view illustrating the principles of the testing apparatus of FIGS. 1 and 4.

Frame 21 may be provided with at least one outrigger arm 35 to support the arm 30 of pendulum impactor 23 in its desired disposition with respect to frame 21 and headform-neck assembly 24, prior to the pendulum impactor 23 being released to pivotally move toward, and into contact with, the headform-neck assembly 24. In the test apparatus 20 of FIGS. 1–3, four outrigger arms 35 are utilized to support and hold pendulum impactor 23 in its first location, prior to being released to pivotally move toward, and contact, headform-neck assembly 24. In this regard, the test apparatus 20' of FIGS. 4 and 5 is substantially the same as that of FIGS. 1–3, with the exception that only a single outrigger arm 35 is illustrated for initially retaining the pendulum impactor 23 in its first location.

As seen in FIGS. 1–3, a winch 36 having an associated cable 37 is mounted to one of the vertical support members 22, and one end of the cable 37 passes upwardly and along one of the outrigger arms 35 through a sheave 38, or other suitable device to a release mechanism 39 suspended from the end of cable 37. Release mechanism 39 may include an eye bolt 41 fixedly secured to the rear face of the impact head 32, and the eye bolt 41 is releaseably engaged by a hook 42 associated with the end of cable 37. Release mechanism 39 may preferably include an air cylinder, or other hydraulic cylinder, 43 which upon activation releases hook 42 from eye bolt 41 in any suitable fashion. A coiled air supply hose 44 may also be suspended from the outrigger arm 35 and disposed about cable 37, as shown in FIGS. 1 and 3. Thus, upon rotating the arm 45 of winch 36, after connecting hook 42 to eye bolt 41, the cable 37 and attached pendulum impactor 23 may be raised to its desired location with respect to frame 21 and headform-neck assembly 24. Upon operation of air cylinder 43, in any suitable manner, hook 42 will be moved to disengage it from eye bolt 41, whereby pendulum impactor 23 may pivotally move with respect to frame 21 toward, and into contact with, headform-neck assembly 24. Of course, any suitable release mechanism could be utilized in addition to that previously described.

With reference to FIGS. 2, 3–8, 14, and 15, the headform-neck base assembly 25 will be described in greater detail. The base assembly 25 is preferably capable of providing adjustment of the disposition of the head-neck assembly 24 in five degrees-of-freedom for the base 50 of the head-neck assembly 24. These adjustments preferably include fore-aft (X), lateral (Y) and up-down (Z) translation, as well as foreaft (Y) and axial (Z) rotation of the head-neck base 50. The adjustment provisions must be lockable and remain fixed throughout testing, as by the use of suitable nuts and bolts 51, 52. The adjustment ranges of the base assembly 25 preferably permit any location on the headform 60 of the head-neck assembly 24 to be impacted from any direction by the center of the impact face 32.

The base 50 shall be located relative to the pendulum face 32 such that the initial point of contact with the helmet 40 is within 10 cm of the base of the pendulum's swing. Plus or minus 10 cm of pendulum arm 30 arc (or swing) will have a negligible effect on the pendulum impactor 23 speed and direction. The base assembly 25 is preferably rigidly connected to a mass of at least 500 kg, which is preferably a concrete slab floor upon which test apparatus 20 is placed.

Figure 8:
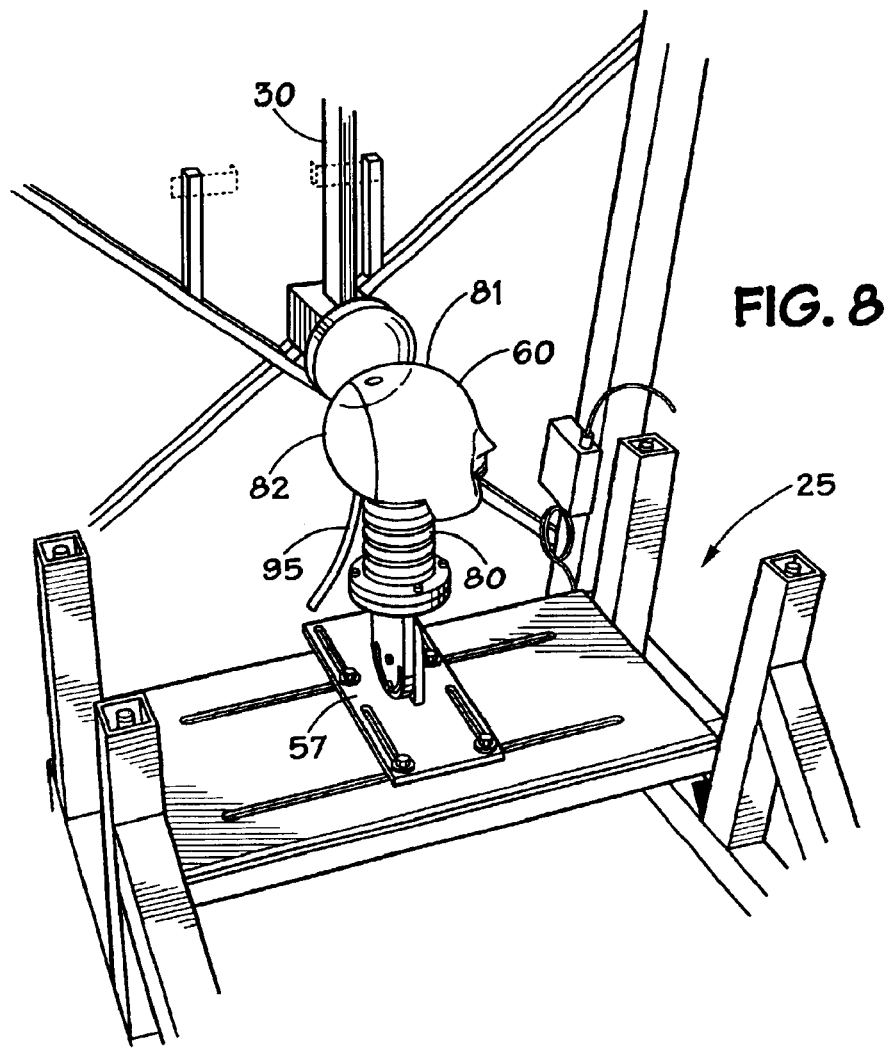
FIG. 8 is a partial perspective view of portions of the testing apparatus of FIG. 1.
Figure 14:
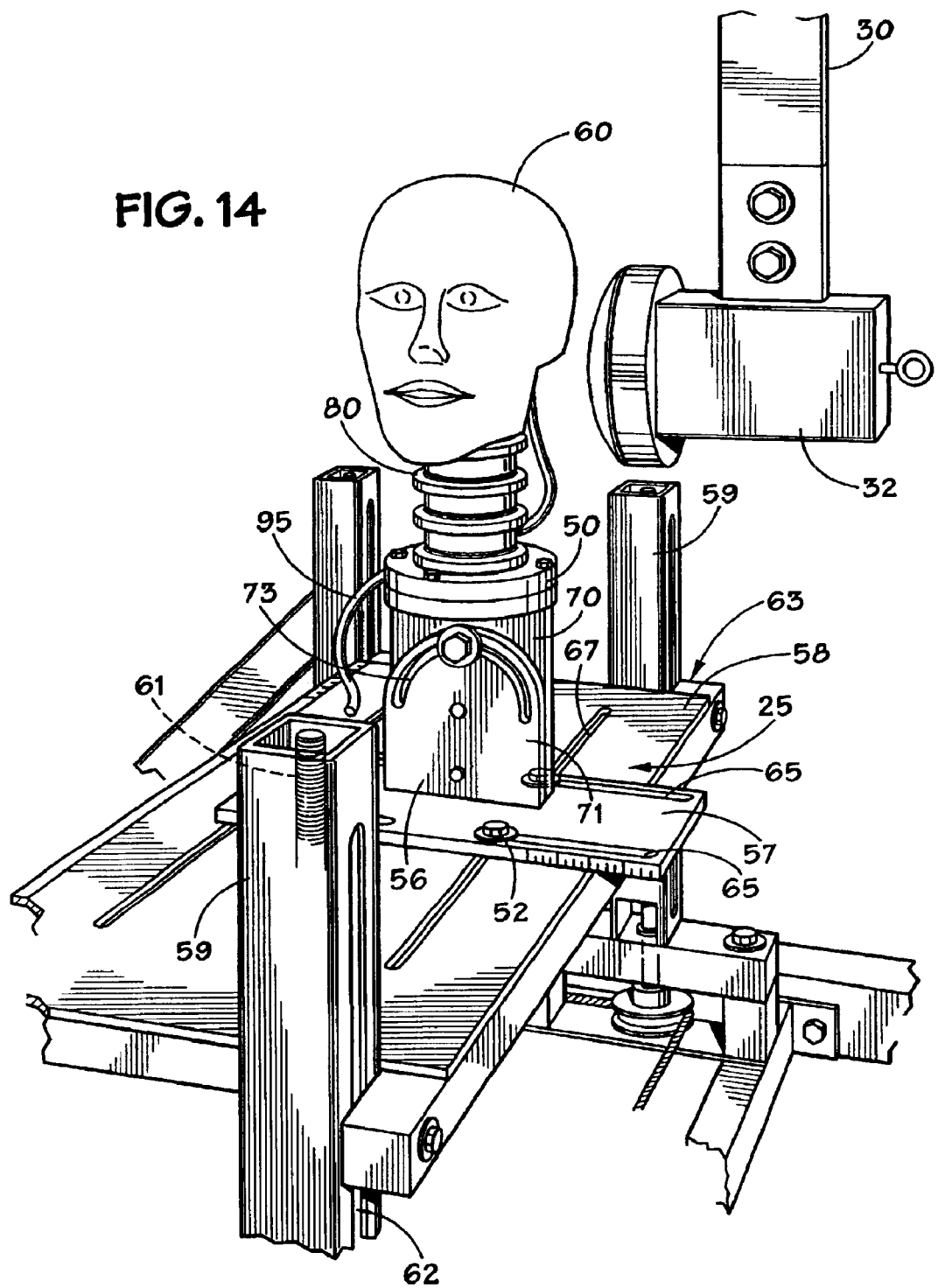
FIG. 14 is another partial, perspective view of the views of the headform of FIGS. 6 and 8.
Figure 15:
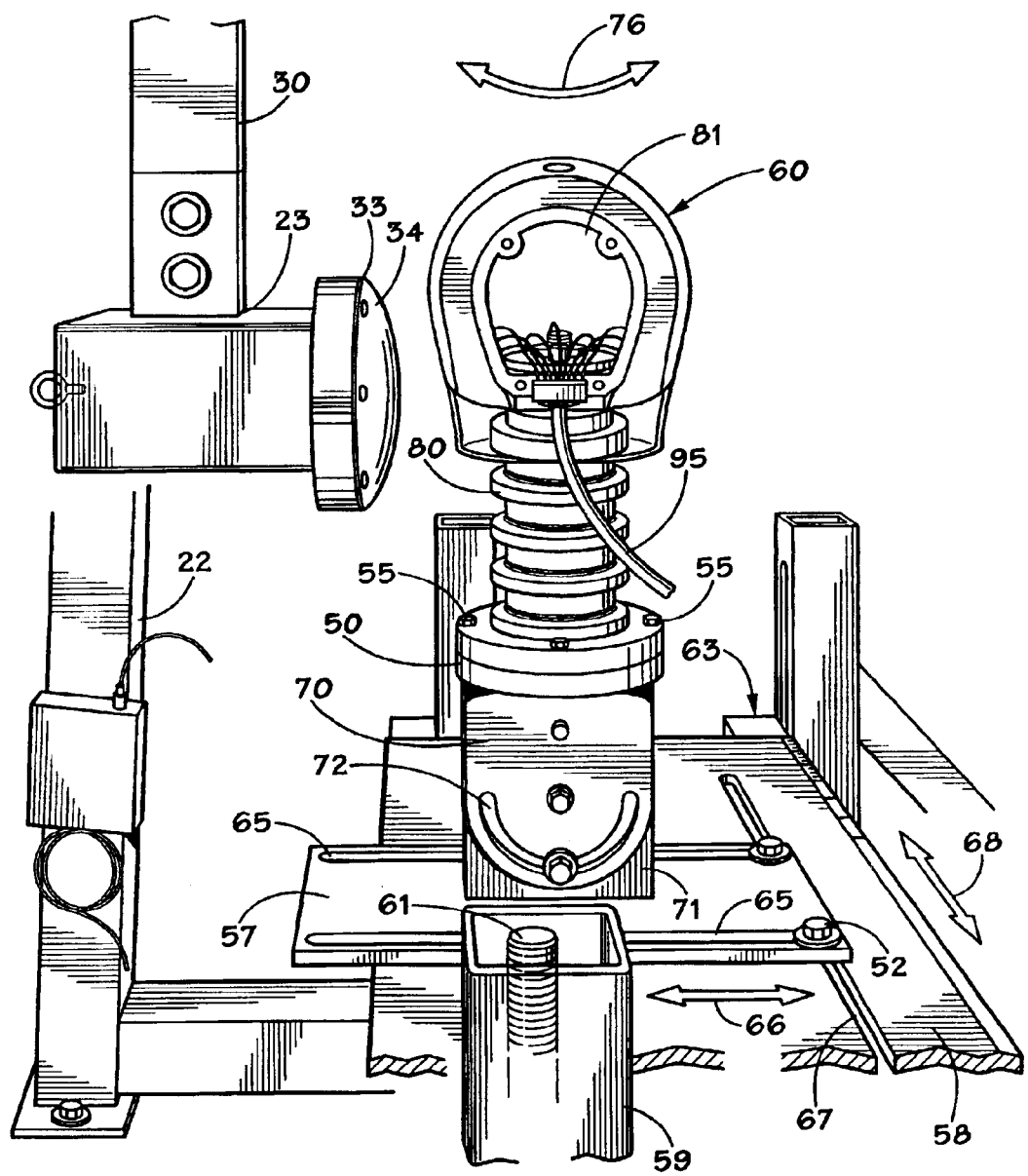
FIG. 15 is a rear view of views of the headform of FIG. 14, with the rear portion of the headform being removed.

With reference to FIGS. 8, 14, and 15, the headform-neck assembly 24 is connected to base 50, as by bolts 55. By adjusting bolts 55, base 50 may be rotated about the longitudinal axis of neck 80. Base 50 is in turn connected to the base assembly 25 by an upstanding bracket assembly 56, which is in turn mounted upon a first horizontal base plate 57, which in turn is associated with a second horizontal base plate 58. The second horizontal base plate member 58 is associated with at least one, and preferably four, upstanding vertical support members 59, one support member 59 being disposed at each corner of the second horizontal base plate member 58. A threaded member 61 is disposed within each of the vertical supports 59. Preferably, four threaded members 61 are provided, and they are interconnected by a chain drive (not shown), whereby upon rotation of any one of the threaded members 61, the second horizontal base plate 58 may be raised or lowered as desired, to properly position the headform 60 of the headform-neck assembly 24 with respect to the impact face 32 of pendulum impactor 23. Each vertical support member 59 has an opening, or slot, 62 extending along the length of each vertical support 59, whereby a bracket member 63 associated with each corner of second horizontal base plate member 58 may pass through the opening 62 and engage the threaded member 61, whereby the desired relative movement between the vertical support 59 and the second base plate member 58 may be provided.

Similarly, upon sliding of the first base plate member 57 with respect to the second base plate member 58, the position of the headform 60 may be adjusted to a desired location. In this regard, first horizontal base plate member 57 has at least one slot 65 formed therein which cooperates with at least one bolt 52 and mating nut. Upon placement, or sliding, of first horizontal base plate member 57 with respect to the second base plate member 58, to its desired location, in the direction of arrows 66, the at least one nut and bolt are tightened to secure base plate 57 to base plate 58. Similarly, a slot 67 is provided in second horizontal base plate member 58, which also cooperates with the at least one bolt 52 and the at least one corresponding nut, whereby first horizontal base plate 57 may be moved in the direction of arrows 67 to also position base plate 57 with respect to base plate 58.

Still with reference to FIGS. 8, 14, and 15, bracket assembly 56 includes at least two plate members 70, 71, each plate member having an arcuate slot 72, 73, and a corresponding nut and bolt 74, 75, whereby the headform-neck assembly 24 may be rotated in the direction of arrows 76 with respect to the horizontal base plate members 57, 58. Preferably, plate member 70 is fixedly secured to the first horizontal base plate member 57, as by welding, and the second plate member 71 is secured, as by welding, to the underside of base 50. Thus, head-neck base assembly 25 functions in the manner previously described to provide the preferred adjustments for the spatial location and disposition of headform 60 with respect to the pendulum impactor 23.

As shown in FIGS. 9, 10, 14, and 15, the headform 60 and neck 80 preferably may be from a Hybrid III 50th percentile male anthropomorphic device (ATD). The headform 60 is preferably machined to provide mounting platforms for acceleration instrumentation to be hereinafter described. The headform 60 may be provided with a standard head skin. A six-axis upper neck load cell may be installed, but it is not specifically required. The neck 80 has an internal neck cable that is preferably tightened to a torque of 10 in-lbs prior to testing. Two layers of ladies' nylon stock stockings may, if desired, be stretched over the assembled headform 60, prior to installation of test helmets 40. The skull 81 and skull cap 82 of headform 60 (FIG. 8) are preferably of one piece aluminum construction with removable vinyl skins. Neck 80 is preferably segmented rubber and aluminum construction with a center cable. The neck 80 accurately simulates the human dynamic moment/rotation flexion and extension response.

Figure 9:
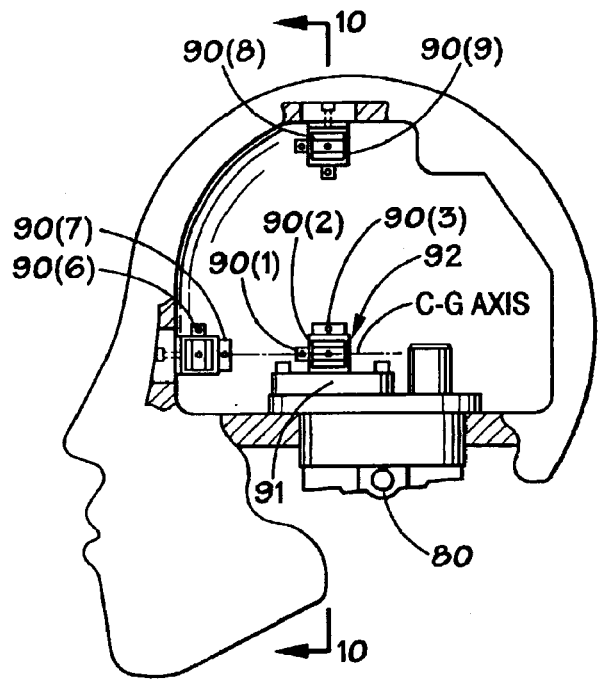
FIG. 9 is a partial cross-sectional view of the headform of FIG. 6.
Figure 10:
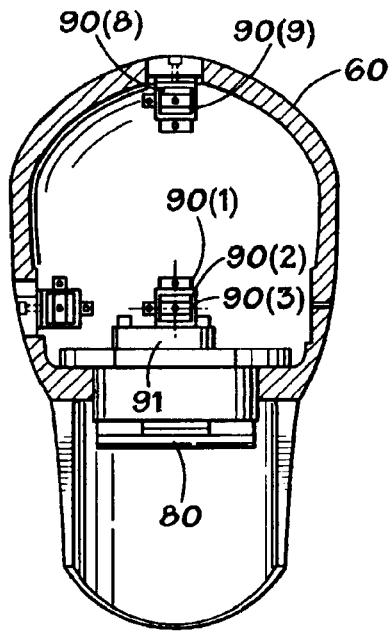
FIG. 10 is a partial cross-sectional view of the headform of FIG. 9 taken along the line 10—10.
Figure 11:
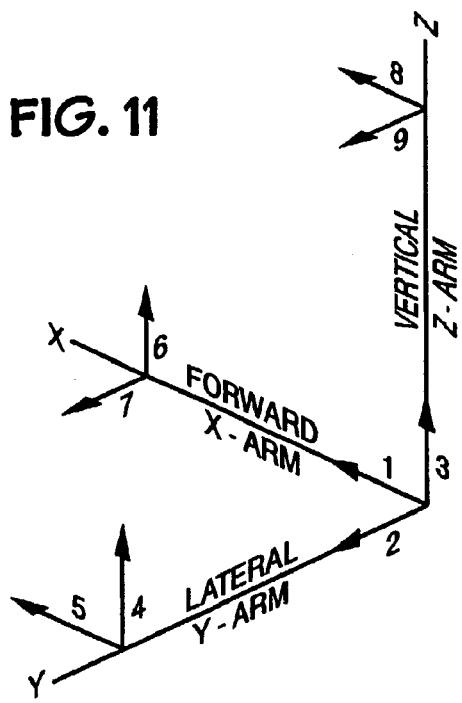
FIG. 11 is graphical depiction of the location of various accelerometers disposed within the headform of FIGS. 9 and 10.

As shown in FIGS. 9–11, the headform 60 includes a nine-accelerometer matrix, in a 3-2-2-2 pattern. The "3-2-2-2" designation refers to the arrangement pattern of accelerometers 90. Three accelerometers 90 are mounted on a common block 91 at the center of gravity 92 of headform 60. Three pairs of accelerometers 90 are mounted outboard directly in front of, directly left of, and directly above this center of gravity block 91. In this manner, comparison may be made between acceleration of the center of gravity 92 and the acceleration of points outboard of the center of gravity 92. The difference in this acceleration, multiplied by the distance between them, is a measure of rotational acceleration. FIG. 11 also illustrates the various axes X, Y, and Z and the location of the nine accelerometers denoted as 1–9. The accelerometers 90 are preferably piezo-resistive, and are capable of withstanding a minimum 1000 G without damage. Alternative rotational acceleration measurement systems may also be used, but they must be proven to have similar measurement capabilities. An example of an acceptable accelerometer is Endevco Model 7264 from Endevco, Inc. of San Juan Capistrano, Calif.

Figure 16:
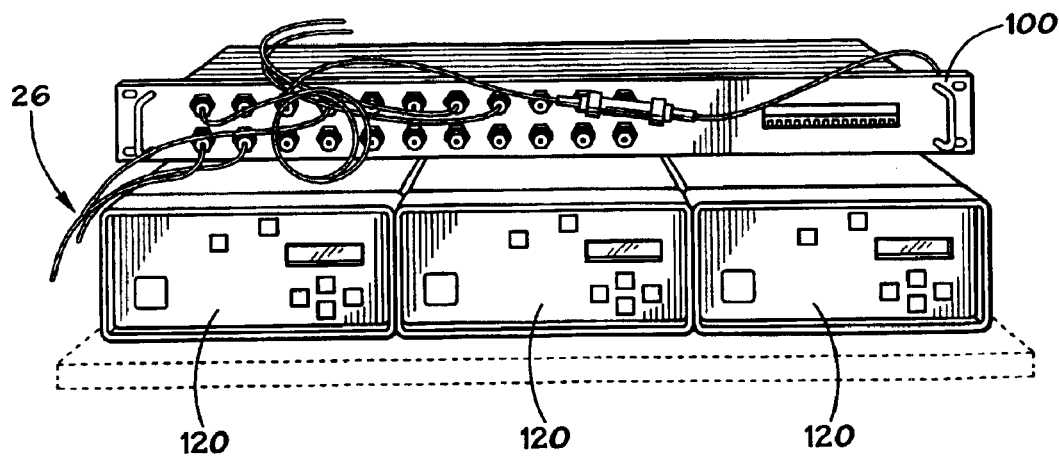
FIG. 16 is a front view of some of the electronic equipment used in connection with the test method and apparatus of the present invention.

As shown in FIGS. 15 and 16, the electronics 26, include a data acquisition system, or data-logger, 100 and shall be capable of recording nine data channels at a minimum 8 kHz (8000 cycles per second) for a minimum of 100 ms, following the practice of SAE J211. Any suitable, commercially available data acquisition system may be used, and it is connected to the nine accelerometers by suitable cabling 95, as shown in FIG. 15. If velocity measurement is calculated by the data acquisition system 100, an additional channel must be provided. All individual acceleration data shall be pre-conditioned by appropriate signal amplifiers 120, such as Endevco Model 136, and CFC 1000 filters, following the practice of SAE J211. A suitable data recording trigger system is provided, such as a signal from the velocity gate or a threshold acceleration level measured by a particular data channel to trigger the system, in conjunction with a percentage pre-capture feature that stores the data that occurred just prior to trigger.

The pendulum impact face 32 velocity is preferably measured at a point within 5 degrees of the base of swing of arm 30, and before pendulum contact is made between impact face 32 and headform 60. Target velocity may be achieved by measuring the height change of the pendulum head 32 from its first position before it is released to point at which it strikes the helmet 40. Using the equation h=(target velocity)/19.62, the h will return the amount that the pendulum impactor 23 must be raised from resting position adjacent headform 60, measured vertically from the laboratory floor. Units for target velocity are in meters per second. Units for height will be in meters. To convert meters to inches, multiply meters by 39.37. At the point within 5 degrees of the base of swing over 99% of the pendulum's 23 final velocity has been achieved. To verify the horizontal distance between the velocity gate and the base of swing, the pendulum length from the pivot to the impact face may be multiplied by 0.0872 (which is sin 5.degree.). For example, a pendulum arm 300 cm long would require the gate to be 300.times.0.0872=26 cm from the base of swing.

Helmets 40 (FIGS. 12 and 13) shall be tested complete, in the condition offered for sale, and the helmet is placed over headform 60 as shown in FIGS. 12 and 13. Pendulum tests shall be conducted with a face mask 110 installed, using the manufacturer's recommended standard attachment method. Preferably the lightest full-face metal wire mask 110 offered by the manufacturer will be installed. The headform 60 shall be oriented such that the neck 80 is vertical. This implies that the head 60 will be inclined in a slight face-up attitude of approximately 5.degree. This is normal for the Hybrid III head-neck assembly 24. For the front hit upon helmet 40, the center of the impact face 32 shall be aligned mid-way laterally, and approximately 71 mm above the head center of gravity 92. For the side hit, the center of the impact face 32 shall be aligned with a point approximately 38 mm vertically above the head center of gravity 92. The pendulum impactor 23 is preferably released from a height to achieve an impact speed of 2.14 m/s.+−.0.04 m/s. For the front hit upon helmet 40, the resultant linear acceleration is preferably 109 G.+−0.5%. The resultant rotational acceleration shall be 9240 rad/s.sup.2.+−0.5%. For the side hit, the resultant linear acceleration is preferably 105 G.+−0.5%. The resultant rotational acceleration shall be 11683 rad/s.sup.2.+−0.5%.

With reference to FIGS. 12 and 13, eight impact sites are preferably utilized. Each site location shall be in horizontal line with the centerline of the impact pendulum face 32, measured while the pendulum arm 30 is at rest at the base of its swing. Impacts are delivered to the rear, rear 45°, side, front 45° and front of the headform 60. In practice, due to the smooth rounded shape of football helmets 40, head-to-head impacts tend to be glancing blows. This is recognized in both the design of the pendulum impactor 32, as well as the final selection of impact sites. In general, the pendulum 23 delivers a more substantial blow to impact sites in the lower regions of the helmet 40, because it becomes more difficult for the pendulum to clear the helmet, and therefore more energy delivered to the headform 60. Additional impacts are delivered in the region of the jaw pad. Impact sites are defined below in relation to two reference systems. The first is the center of gravity of the headform 60. On the Hybrid III headform 60, the center of gravity 92 lies directly between small holes in the head skin, on the left and right sides, in the region where ears would be. The elevation of this point becomes the first reference. The second reference system is based on the pivot axis of the Hybrid III neck 80. Some impacts may include contact with the face mask 110. Maintaining the neck 80 vertical gives the headform 60 a slight chin-up attitude, making traditional headform reference planes (such as the basic plane and coronal plane) inappropriate.

Site I (center of gravity)—Neck is oriented vertical. Lateral impact directed through the center of gravity of the headform.

Site D (high side)—Neck is oriented vertical. Lateral impact directed 20 mm behind and 64 mm above center of gravity.

Site T (front side)—Neck is oriented vertical. Lateral impact directed 52 mm forward and 15 mm below center of gravity.

Site 1I (front earflap)—Neck is oriented vertical. Lateral impact directed 43 mm forward and 54 mm below center of gravity.

Site N (rear)—Neck is oriented vertical. Rear impact, centered on the headform, directed 15 mm below center of gravity.

Site H(rear boss)—Neck is oriented vertical. Neck is pivoted on its vertical axis 45° from site N.

Site V(front boss)—Neck is oriented vertical. Neck is pivoted on its vertical axis 45° from site D.

Site E (front)—Neck is inclined forwards 7.5°. Front impact, centered on headform, 103 mm above the center of gravity.

The testing method of the present invention will now be described. Each helmet shall be impacted once at each of the sites described in connection with FIGS. 12 and 13. The base assembly 25 and neck 80 are adjusted to align the desired impact site. The helmet 40 is placed upon the headform 60, and the retention system, such as a conventional chin strap (not shown), is fastened according to manufacturers instructions. A NOCSAE helmet-positioning tool may be used to establish the wearing attitude. The pendulum impactor 23 is raised to an appropriate height to achieve the target impact speed and released. The data from the nine accelerometers 90 is collected and recorded. The helmet 40 shall then be completely removed, inspected and re-installed for the next test. Any damage to helmet 40 or face mask 110 shall be noted. Damaged face masks 110 shall be replaced with an identical model prior to further testing.

Immediately after impact, the filtered data from each accelerometer 90 shall be recorded digitally. This data may be processed at any time thereafter to calculate the linear and rotational accelerations in the X, Y, Z and resultant directions; however, it is recommended that this processing occur automatically with each impact, such that any data errors may be uncovered before testing is completed. The raw acceleration data from the three enter of gravity accelerometers 90 is also "corrected" in the algorithm used. It is physically possible to place three accelerometers simultaneously at the precise center of gravity 92, and so they are mounted on the X, Y and Z axes as close as possible to the center of gravity 92. However, under rotational acceleration conditions, the distance between the accelerometer data the center of gravity will introduce centripetal acceleration into the signal. While this error is very small, the algorithm makes appropriate corrections. The algorithms for computation of linear and rotational accelerations are available from the NHTSA, NHTSA DoT 808 282. Transformation of the Nine Accelerometer Package (NAP) Data for Replicating Headgear Kinematics and Dynamic Loading, August 1995. The linear and rotational acceleration data is then processed to produce the overall power, from which the maximum value is found, resulting in a maximum Head Impact Power Index or the HIPmax.

$$\text{Power} = P = \Sigma m \bar{a} \cdot \bar{v} + \Sigma \bar{I\alpha} \cdot \bar{\omega}$$

where:
- $\bar{a}$ = linear acceleration (m/s²)
- v = linear velocity (m/s)
- I = mass moment of inertia (Nms²)
- m = mass (kg) The sub-routines used to calculate the HIPmax are preferably in LABVIEW® software format, and may be obtained from Biokinetics and Associates Ltd., or other suitable computer software may be utilized that can perform the foregoing calculations. When the coefficients are set equal to the mass and appropriate mass moments of inertia for the Hybrid III head, the expression becomes:

$$HIP = 4.50 a_x \int a_x dt + 4.50 a_y \int a_y dt + 4.50 a_z \int a_z dt +$$
$$0.016 \alpha_x \int \alpha_x dt + 0.024 \alpha_y \int \alpha_y dt + 0.022 \alpha_z \int \alpha_z dt$$

A helmeted Hybrid III head, assembled with neck, is impacted by the weighted pendulum impactor 23. The head is instrumented to measure linear and rotational acceleration, and the data is processed to calculate the maximum HIP or HIPmax. The calculation of maximum impact power (HIP) transmitted to the test headform is intended to determine the effectiveness of a headgear in preventing injury to the football player. It is recommended that the pendulum speed be 5.4 m/s, measured at the impacting face. It is recommended that the maximum HIP not exceed 12.8 kW for the impact forces at the sites previously described.

We claim:

1. A method for testing a helmet comprising the steps of:
   placing a helmet upon a headform having a plurality of accelerometers to measure linear and rotational acceleration;
   striking the helmet with a weighted pendulum to impart an impact force, and
   measuring linear acceleration and rotational acceleration of the headform caused by the impact force.

2. The method of claim 1, wherein the pendulum is operably connected to a support frame.

3. The method of claim 1, including the step of utilizing a neck with the headform to provide a headform-neck assembly.

4. The method of claim 3 wherein the headform-neck assembly is disposed upon an adjustable base.

5. The method of claim 4, including the step of adjusting the base to selectively position the headform and the helmet, wherein the pendulum strikes a specific region of the helmet.

6. The method of claim 4, including the step of rotating the base, wherein the pendulum strikes a specific region of the helmet.

7. The method of claim 1, wherein the pendulum an impact head with a domed spherical outer surface which strikes the football helmet.

8. The method of claim 1, wherein the plurality of accelerometers comprises nine accelerometers positioned within the headform.

9. The method of claim 1, including the step of striking the helmet at a plurality of locations on an outer surface of the helmet.

10. The method of claim 7, including the step of providing the domed spherical outer surface with a radius of curvature which generally corresponds to the radius of curvature of an upper portion of the helmet.

11. The method of claim 7, including the step of providing a layer of plastic material upon the domed spherical outer surface, the plastic material generally corresponding to the same material of which the helmet is made.

12. The method of claim 1, wherein the helmet is struck by the weighted pendulum at a speed of approximately 5.4 m/s.

13. An apparatus for testing a football helmet, having an outer surface and an upper portion comprising:
   a pendulum arm having first and second ends;
   the first end of the pendulum arm being mounted for rotational movement;
   a weight disposed on the second end of the pendulum arm; and
   a headform disposed upon a base, the headform including a plurality of accelerometers, adapted to measure linear head acceleration and rotational head acceleration by an impact force upon the headform, whereby the football helmet may be tested after the football helmet is placed on the headform and struck with the weight.

14. The apparatus of claim 13, including a neck associated with th headform to provide a headform-neck assembly, the headform-neck assembly being disposed the base.

15. The apparatus of claim 13, wherein the weight is an impact head.

16. The apparatus of claim 15, wherein the impact head has a domed spherical outer surface which is adapted to strike the football helmet.

17. The apparatus of claim 16, wherein the domed spherical outer surface has a radius of curvature which generally corresponds to the radius of curvature of the upper portion of the football helmet.

18. The apparatus of claim 16, wherein a layer of plastic material is disposed upon the domed spherical outer surface, the plastic material generally corresponding to the same material of which the football helmet is made.

19. The apparatus of claim 13, wherein the first end of the pendulum arm is disposed above the football helmet to be tested.

20. The apparatus of claim 13, wherein the pendulum has a minimum length of approximately 200 cm.

21. The apparatus of claim 13, wherein the headform is adjustably mounted with respect to the base, so that when a helmet to be tested is placed on the headform to struck by the weight, the helmet may be struck at any desired location upon the outer surface of the football helmet.

22. The apparatus of claim 13, wherein the headform is adjustably mounted with respect to the base to permit movement of the headform with respect to the base in plurality of directions.

23. An apparatus for resting a helmet, the apparatus comprising:
   a support frame having a pendulum arm with a weighted end and a headform configured to receive a helmet; and,
   a plurality of accelerometers positioned within the headform to measure the linear and rotational acceleration resulting from a strike of the weighted end.

24. The testing apparatus of claim 23, wherein the headform is adjustably connected to the support frame, and wherein the headform can be selectively positioned such the pendulum strikes a specific region of the helmet.

25. The testing apparatus of claim 23, wherein the headform is connected to an adjustable base that can be selectively positioned such that the a specific region of the helmet is struck by the pendulum.

26. An apparatus for testing a sports helmet, the apparatus comprising:
- a support frame;
- a weighted pendulum operably connected to the support frame;
- a headform affixed to the support flame and configured to receive the helmet, the headform having a plurality of accelerometers to measure the acceleration resulting from the weighted pendulum striking the helmet.

27. The testing apparatus of claim 26, wherein the accelerometers are positioned within a cavity of the headform.

28. The testing apparatus of claim 27, wherein the headform includes at least three accelerometers positioned at the center of gravity of the headform.

29. The testing apparatus of claim 27, wherein at least two accelerometers are positioned in a frontal region of the headform.

30. The testing apparatus of claim 27, wherein at least two accelerometers are positioned in an upper region of the headform.

31. The testing apparatus of claim 27, wherein at least two accelerometers are positioned in a side region of the headform.

32. The testing apparatus of claim 26, wherein the accelerometers are operatively connected to a data logging and computation system that calculates the acceleration.

33. An apparatus for testing a sports helmet comprising:
- a pendulum arm having first and second ends, the first end of the pendulum arm being mounted for rotational movement;
- a weight disposed on the second end of the pendulum arm; and,
- a headform disposed upon a base, the headform configured to receive the helmet, the headform comprising an accelerometer to measure acceleration of the headform.

* * * * *